United States Patent [19]

Zaccari et al.

[11] Patent Number: 4,664,772
[45] Date of Patent: May 12, 1987

[54] INSERTION PROBE SYSTEM FOR CONTINUOUS MEASUREMENT OF PH LEVEL IN PROCESS LINES

[75] Inventors: Neil J. Zaccari, Boltan Landing; Nick J. Viscovsky, Monroe, both of N.Y.

[73] Assignee: International Paper Company, New York, N.Y.

[21] Appl. No.: 696,564

[22] Filed: Jan. 30, 1985

[51] Int. Cl.⁴ .......................................... G01N 27/46
[52] U.S. Cl. .................................. 204/400; 204/286; 204/297 R; 204/416; 204/420; 204/433
[58] Field of Search ................... 204/400, 416–420, 204/286, 297 R, 433

[56] References Cited

U.S. PATENT DOCUMENTS

| | | | |
|---|---|---|---|
| 2,884,365 | 4/1959 | DeBolt et al. | 204/420 |
| 3,341,443 | 9/1967 | Leonard . | |
| 3,647,666 | 3/1972 | Simon et al. . | |
| 3,717,565 | 2/1973 | Doyle, Jr. . | |
| 3,806,440 | 4/1974 | Gray et al. | 204/420 |
| 3,882,011 | 5/1975 | Hines et al. . | |
| 4,008,141 | 2/1977 | Kotani et al. | 204/433 |
| 4,012,308 | 3/1977 | Jerrold-Jones et al. | 204/420 |
| 4,016,063 | 4/1977 | Radnoti . | |
| 4,112,352 | 9/1978 | Barben | 204/433 |
| 4,118,663 | 10/1978 | Barben, II . | |
| 4,128,468 | 12/1978 | Bukamier . | |
| 4,166,020 | 8/1979 | Trampert . | |
| 4,196,384 | 4/1980 | Willenbrock et al. . | |
| 4,202,749 | 5/1980 | Phelps et al. | 204/420 |
| 4,333,812 | 6/1982 | Bukamier et al. . | |
| 4,383,908 | 5/1983 | Phelps et al. | 204/433 |
| 4,447,775 | 5/1984 | Breuker et al. . | |
| 4,459,199 | 7/1984 | Fletcher, III . | |

OTHER PUBLICATIONS

Sensorex Bulletin 410, four pages, copyrght 1981, distributed by Sensorex, 11661 Seaboard Circle, Stanton, Calif.

(undated) *TBI Manual* entitled "Measurement of Pulp Stock pH and Conductivity with TBI 'Hot Tap' Sensors", distributed by TBI, 2175 Lockheed Way, Carson City, Nev. 89701.

*Primary Examiner*—T. Tung
*Attorney, Agent, or Firm*—Walt Thomas Zielinski; Martin P. Hoffman

[57] ABSTRACT

A sensor system for measuring the pH level in a process flow pipe, such system utilizing a sensing electrode that fits within, and is protected by, a rugged cylindrical metallic sheath. The sensing electrode is slid by an insertion tube through a ball valve into the process flow pipe. Two spaced collars with two pairs of restraint cables cooperate to retain the sensor system in alignment during the insertion procedure. After insertion, the sensor system is held in position by the pair of shorter restraint cables extending between the collars, while a compression nut is advanced onto a tube fitting to mechanically join the insertion shaft to the sensor system.

7 Claims, 4 Drawing Figures

INSERTION PROBE SYSTEM FOR CONTINUOUS MEASUREMENT OF PH LEVEL IN PROCESS LINES

BACKGROUND OF THE INVENTION

The instant invention relates generally to an instrument for measuring the pH level of fluids of high consistencies, slurries, and the like, passing through a pressurized process pipe. More particularly, the instant invention relates to mechanisms for protecting the instrument from harm attributable to the material being conveyed by the process pipe and for introducing the instrument into the process pipe.

The paper industry has utilized diverse probe-like instruments for measuring the pH of the pulp stock in pulp and paper mills. The pH level, which is a measure of the acidity or alkilinity of the product, is effectively determined by a pH probe. Most known pH probes employ a glass electrode and a reference electrode, generally retained within the same housing and identified as a "combination" electrode. The glass electrode includes a pH sensitive glass membrane attached to a glass tube containing a metal electrode and a saturated aqueous solution, such as potassium chloride, or a metal-metal salt, such as silver-silver chloride. The reference electrode is retained within a space filled with the same type of solution and has a porous wall. The electrodes function to generate an electrical signal which is proportional to the pH level in the fluid being measured. The electrical signal, when appropriately amplified, may be used to adjust operating parameters upstream or downstream of the probe.

Representative pH probes are disclosed in U.S. Pat. No. 4,112,352, granted to T R. Barben II, U.S. Pat. No. 4,008,141, granted to H. Kotani et al, and U.S. Pat. Nos. 4,202,749 and 4,383,908, both granted to T. C. Phelps et al.

Known pH probes functioned satisfactorily under low pressure flow conditions when the fluid is of low consistency (percent solid matter), or when employed to measure the pH in an off-line or batch process. However, known pH probes were found to be susceptible to breakage and clogging, and short service life, when exposed to harsh, on-line, continuous operating conditions, such as those encountered in pulp and paper mills, chemical processing plants, or the like. The component found to be most prone to failure proved to be the glass sensing electrode which projects into the stream flowing through the process pipe.

The glass pH sensing electrode 10 shown in FIG. 2 of the Barben, II patent projects beyond the rigid cylindrical housing that contains the other components of the instrument. A series of toroidal hardwood plugs 20 fit within the cylindrical housing and serve as the porous junctions of the reference electrode. The end of the electrode 10, however, is unprotected and unsupported, and has been easily broken by solid objects that may normally, or inadvertently, be in the flowing process stream.

Kotani et al recognizes the fragile nature of glass sensing bulb 5 which includes a glass membrane 8, and provides a pH probe that allows the sensing bulb to be easily replaced. A side wall 17 of a strong, yet porous, material is utilized, as noted in column 2, lines 24–35 of such patent, to surround a major portion of the body of the probe. A cap 14 with a central bore receives electrode 5, and the projecting flanges surround the glass membrane.

However, under field conditions and particularly when measuring pH values in a stream with high solids concentration, or high consistency, such as wood pulp slurry, the pulp can accumulate into a solid mass between the flanges and sensing bulb and eventually will interfere with the accurate determination of pH. Thus the pH probe must be removed from the process stream frequently to permit cleaning or electrode replacement which is a costly and counterproductive procedure, particularly when the high levels of paper mill production dictate continuous, on-line pH monitoring, whenever possible.

Phelps et al '749 and Phelps '908 disclose a pH probe system that may be removably installed in-line in a pressurized pipe line to determine the pH of the fluid flowing therethrough; see FIG. 1 in each patent. The probe is coated with a smooth adherent coating 37, such as woven filaments of glass impregnated with a plastic resin and a hardener. The coating defines an elongated sheath with a uniform, round circumference. A sensor head with a glass electrode tip 38A is shown in FIG. 2 of each patent. A protector shield 41 fits over the sensor head and includes a flange 42 positioned in the direction of the flow in order to protect the sensor portion of the probe.

The protector shield shown in the Phelps et al patents, however, requires the shield for the pH probe system be properly oriented upon insertion into the process flow line, and this orientation may not be readily attained. Additionally, during purging or draining or other conditions leading to reverse flows within the process pipe, the flange will be ineffective and the sensing electrode will be subjected to reversely directed forces, or impacted by solid objects, which may break or otherwise damage the sensing electrode. Furthermore, the flange on the protector shield may cause vortex shedding or other flow disturbances, such as stagnation of flow on the downstream side of the flange. Such disturbances contribute to the accumulation of solids or pulp between the flange and the sensing electrode. This may cause formation of a dewatered mass that may eventually cover part, or all, of the sensing electrode so that the pH measurement will not accurately reflect the actual pH of the process stream.

SUMMARY

In view of the structural deficiencies and operational limitations of known pH sensors and systems employing such instruments, the instant invention contemplates a pH probe system characterized, inter alia, by a metal sheath that surrounds a replaceable glass electrode and strengthens the entire assembly. Consequently, the probe system is well suited for use in continuously monitoring operations for process pipes and effectively determining pH values. The probe system is versatile and can be utilized with a wide variety of pressurized, or non-pressurized, flows of different consistencies.

Furthermore, the metal sheath receives, and surrounds, the body of the electrode, thereby precluding the accumulation of solids, pulp or other debris therebetween.

The pH probe is readily inserted into a process flow line through a ball valve. The pH sensor is equipped with four restraint cables that assist in (1) preventing probe ejection during insertion, (2) inserting the probe to the proper depth to achieve representative readings, and (3) retaining the assembly firmly secured in fixed position until a retaining nut is secured in fixed position.

The instant sensor system augments known pH probe instruments by the addition of a protective sheath, a tube fitting, a pair of collars with eye-bolts secured thereto, restraint cables and a retaining nut. The tube fitting is secured to the ball valve, and one of the collars fits thereover. The resultant system is easy to install and service, does not require specific orientation of the protective sheath, and thus minimizes down time and service costs. Furthermore, the system, particularly the protective sheath, insures that the glass electrode is not damaged by solid objects in the flowing process stream or by shear forces caused by flowing high consistency fluids or slurries.

Numerous other advantages attributable to the instant assembly will become readily apparent to the artisan when the appended drawings are construed in harmony with the ensuing description.

DETAILED DESCRIPTION OF THE DRAWINGS

Figure 1:
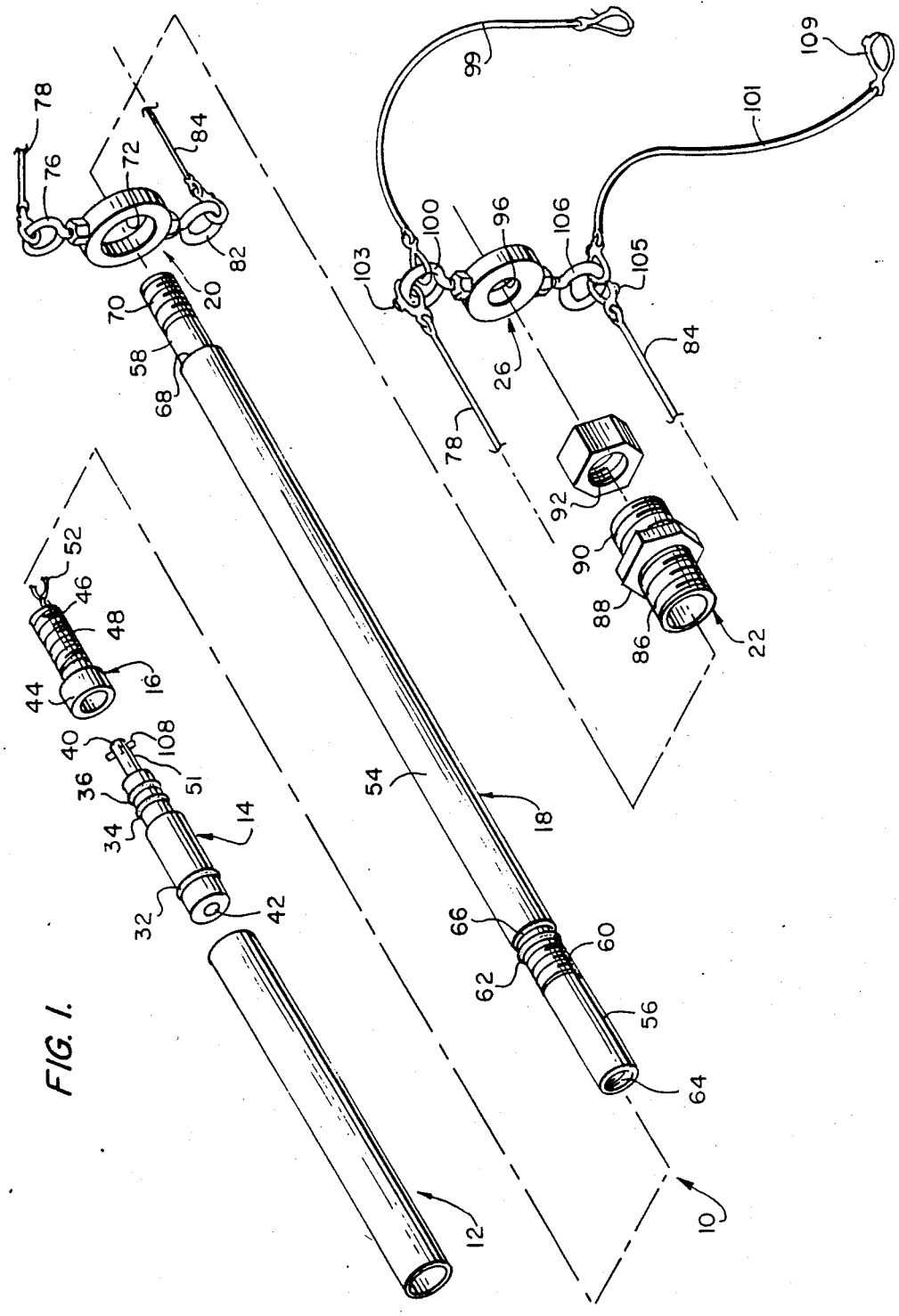
FIG. 1 is an exploded perspective view of a pH sensor system constructed in accordance with the principles of this invention.
Figure 2:
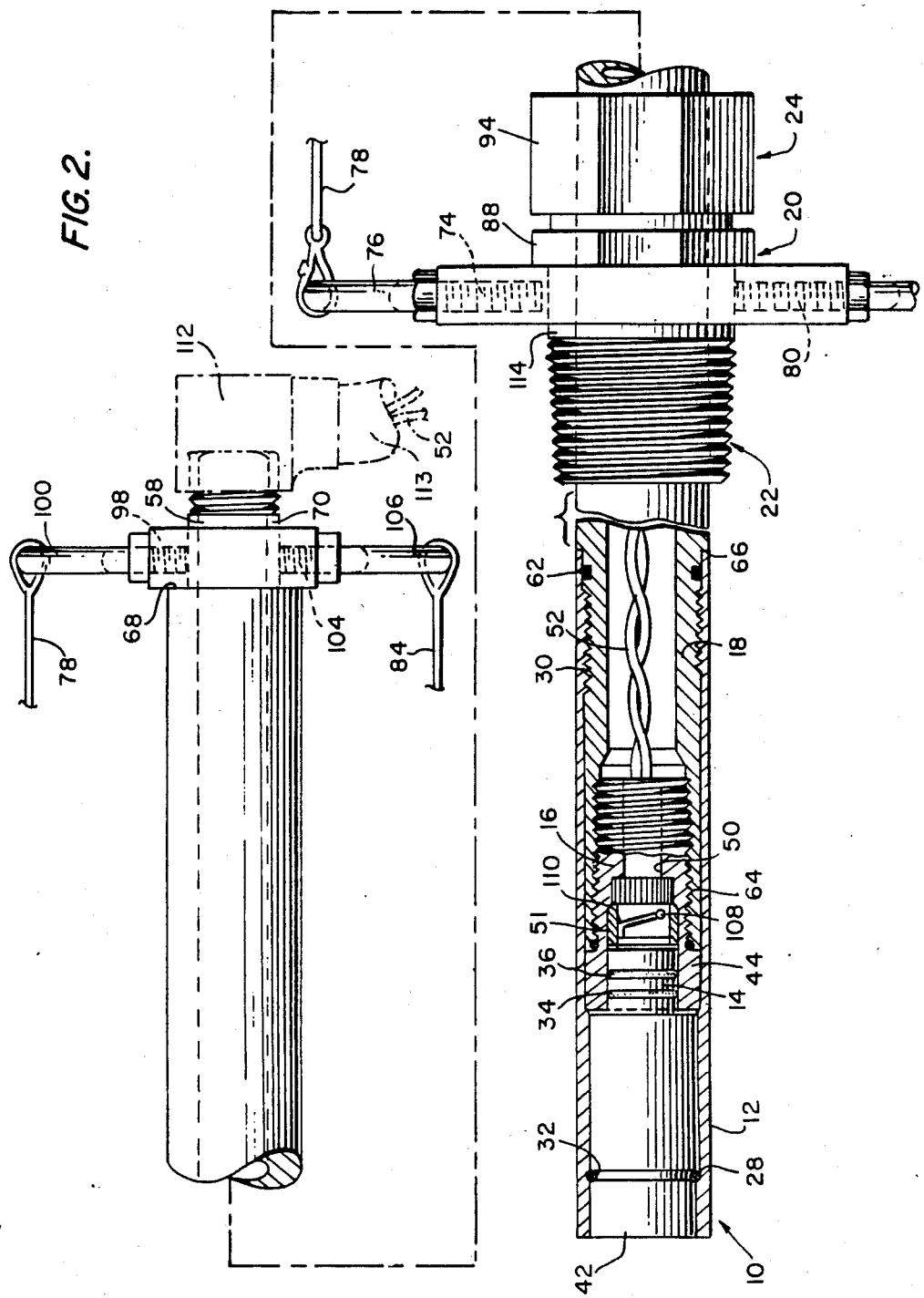
FIG. 2 is a side elevational view of the pH sensor system in assembled condition, such view being taken on an elongated scale.

Referring now to the drawings, FIGS. 1 and 2 show a pH sensor system 10 embodying the principles of the instant invention. The system 10 includes a protective sheath 12, a pH electrode 14, an electrode holder assembly 16, an elongated insertion shaft 18, a first collar 20, a tube fitting 22, a retaining nut 24, and a second collar 26. FIG. 1 shows the components of the system 10 prior to assembly, while FIG. 2 shows the components in assembled condition.

Sheath 12 is a continuous, cylindrical rigid stainless steel member that surrounds and protects electrode 14 against the high consistency pressurized flow, with entrained debris, etc., found in process pipes. A step 28 is formed in the interior surface of the sheath, and internal threads 30 are defined near the rear end of the sheath. A first O-ring 32 encircles the cylindrical body portion of electrode 14, and second and third O-rings 34,36 encircle the smaller rearwardly extending shank 38. A male BNC connection 40 is situated at the end of electrode 14 remote from the flat ion-permeable pH sensing surface 42. Electrode 14 is a combination electrode and further includes a reference electrode that is sealed, and gel-filled; such reference electrode is retained within the interior of the electrode body and is not shown in the drawing.

Electrode 14 is of known design, and is presently available from Innovative Sensors, Inc. of Anaheim, Calif. and Sensorex Corp. of Stanton, Calif. Electrode 14 is readily removable for maintenance or replacement because of the use of a twist lock BNC connector and is compatible with the electronic circuitry utilized by most pH meters. Furthermore, the flat profile of the pH sensing glass membrane 42 precludes damage by solid objects flowing by in the process stream. It is not subject to flow induced shearing forces or stresses that damage bulbous type pH glass membranes.

Electrode holder assembly 16 includes an enlarged collar 44 and a cylindrical shank 46 with external threads 48. A bore 50 extends axially through the interior of the holder assembly 16 so that the electrical leads 52 can pass therethrough. The electrical leads 52 are terminated in a female BNC "twist lock type" connector, 51, that is secured in the bore 50 at the collar 44. Also contained in bore 50, behind the female BNC connector 51, is a thermocompensation resistor (not shown) with electrical leads (not shown). The thermocompensation resistor is potted in place with epoxy and is used in conjunction with external pH signal amplifiers to adjust the pH signal to eliminate the effects of temperature on the voltage generated by the pH electrode.

Elongated insertion shaft 18 is a rigid, hollow cylindrical metallic member comprising a central body 54, a first end section 56, and a second end section 58. The end sections are slightly smaller in diameter than the central body 54. External threads 60 are defined near the intersection of end section 56 and body 54, and an O-ring 62 fits into an annular groove defined on the exterior surface of end section 56. Internal threads 64 are defined within end section 56, and a shoulder 66 marks the intersection of end section 56 and body 54. Another shoulder 68 marks the intersection of the end section 58 and body 54, and external threads 70 are formed near the rearmost end of section 58.

First collar 20 is annular in shape, and the internal diameter of its central opening 72 is slightly greater than the diameter of the leading section of tube fitting 22. A first bolt 74 is secured within a radially extending bore in collar 20. An enlarged eye 76 is defined at the upper end of the bolt 74, and one end of a first restraint cable 78 is secured to eye 76. A second bolt 80 is secured within another radially extending bore in collar 20, so that bolts 74 and 80 are disposed diametrically opposed to one another. An enlarged eye 82 is defined at the upper end of bolt 80, and one end of second restraint cable 84 is secured to eye 82.

Tube fitting 22 comprises a tapered lead section 86, an intermediate shoulder 88, and a tail section 90. Several wrench flats are formed around the periphery of shoulder 88, and sections 86 and 90 are externally threaded. The diameter of the cylindrical bore extending through fitting 22 is greater than the external diameter of insertion shaft 18. An annular groove and O-ring (both not shown) are located on the internal diameter of the cylindrical bore at tail section 90 to create a fluid tight seal between the cylindrical bore and the external diameter of shaft 18. Retaining nut 24 has internal threads 92, and wrench flats 94 are defined about its periphery. A split ring collar (not shown) is located in retaining nut 24. The split ring collar is a thin metal tube that is split at one point along its entire axial length. The split ring collar has annular serrations both on its inside and outside diameters which grab the insertion shaft and an internal unthreaded section of retaining nut 24 when nut 24 is tightened sufficiently. The retaining nut and split ring collar secure the insertion shaft to tube fitting 22.

Second collar 26 is annular in shape, and the internal diameter of its central opening 96 is slightly greater than the diameter of end section 58 on insertion shaft 18. The central opening 96 in collar 26 is smaller than the central opening 72 in collar 20, so that the collars are distinguishable. A first bolt 98 is secured within a radially extending bore in collar 26. An enlarged eye 100 is defined at the upper end of bolt 98, and one end of third restraint cable 99 is secured to eye 100. A second bolt 104 is secured within another radially extending bore in collar 26, so that bolts 98, 104 are disposed diametrically opposed to one another. An enlarged eye 106 is defined at the upper end of bolt 104, and one end of fourth restraint cable 101 is secured thereto.

The four restraint cables 78,84,99 and 101 are properly divided into two pairs of cables, specifically, first and second cables 78,84 and third and fourth cables 99 and 101. One end of cable 78 and cable 84 is permanently joined to first collar 20, while one end of cable 99 and 101 is permanently joined to second collar 26. Although the relative lengths of the cables cannot be discerned from FIGS. 1 and 2, cables 78,84 are identical in length but are considerably longer than cables 99,101, for reasons that will become apparent with regard to the insertion of the sensor system. Shorter restraint cables 99 and 101 are also equal in length to each other.

A spring loaded clip 103 is attached to the free end of restraint cable 78, and an identical spring loaded clip 105 is attached to the free end of companion restraint cable 84. A spring loaded clip 107 is attached to the free end of restraint cable 99, and an identical spring loaded clip 109 is attached to the free end of restraint cable 101.

Clips 103,105 are employed to secure restraint cables 78,84 between first collar 20 and second collar 26 during the insertion process. After the insertion process has been completed, clips 103,105 may be disengaged so that restraint cables 78,84 are ineffective. Clips 107,109 are employed to secure cables 99,101 between first collar 20 and second collar 26 after the insertion process. The shorter restraint cables 99,101 maintain the sensor assembly in operative relationship within the process pipe for accurately determining the pH level. The electrical leads 52 of holder assembly 16 are threaded through the bore of shaft 18 starting at end section 56. The external threads 48 on shank 46 of holder assembly 16 are screwed into engagement with the internal threads 64 formed within the bore of end section 56 of insertion shaft 18.

Male BNC connector 40 both electrically and mechanically joins electrode 14 to the female BNC connector 51 situated inside electrode holder assembly 16. The male BNC connector is guided and removably locked in place by pins 108 protruding from the external surface of BNC connector 40 that ride within grooves 110 (one shown) in the walls of the female BNC connector. Such a pin and slot connection enables the electrode to be easily inserted, locked in place and removed, when necessary. Other couplings could also be utilized that can perform the same function.

The protective sheath 12 is slid over electrode 14 and threads 30 on the interior of protective sheath 12 and screwed into engagement with threads 60 on the exterior of end section 56 of insertion shaft 18. The sheath is tightened against shoulder 66 so that an almost unbroken surface is formed. The external diameter of sheath 12 and insertion shaft 18 are identical so the resultant assembled probe will have one continuous exterior diameter along its axial length except for the external threads 70 at end section 58 of shaft 18. O-ring 62 augments the sealing engagement between the sheath and the insertion shaft. O-ring 32, attached to electrode 14, is seated against step 28. O-rings 32,62 provide assurance that process fluid, debris or other substances do not penetrate the interior of system 10. In such a fashion, the sheath 12 protects the electrode 14, the BNC coupling 40,51, and the electrode holder assembly 16 from transverse shearing forces produced by the flow in the process pipe and from damage that would be caused by impacts by solid objects flowing through the pipe. It is noted that the insertion shaft 18 is several inches in length, and is considerably larger than the other components of sensor system 10. Consequently, in order to accommodate the size of the shaft, portions have been broken away in FIG. 2.

The diameter of the internal bore of tube fitting 22 is greater than the external diameter of insertion shaft 18, so that the insertion shaft may be moved axially through the tube fitting. The lead section 86 is threaded and is tapered, and a land 114 is formed intermediate the threads on lead section 86 and the shoulder 88. First collar 20 is slid over lead section 86 of fitting 22 until the collar abuts against shoulder 88. Clearance is provided between opening 72 and the exterior of land 114 to allow first collar 20 to rotate for reasons to become evident later. Retaining nut 24 has not yet been utilized.

Second collar 26 is slipped over the external threads 70 on end section 58 of insertion shaft 18 until the collar abuts against shoulder 68. The internal diameter of opening 96 is selected to provide sufficient clearance to allow second collar 26 to rotate while on end section 58 of insertion shaft 18 for reasons to become evident later. Conduit 112, indicated in dotted outline, is screwed into engagement with the external threads 70. Flexible conduit 113, shown broken away, is used to protect the signal wires 52 on their run to a pH signal amplifier (not shown).

Figure 3:
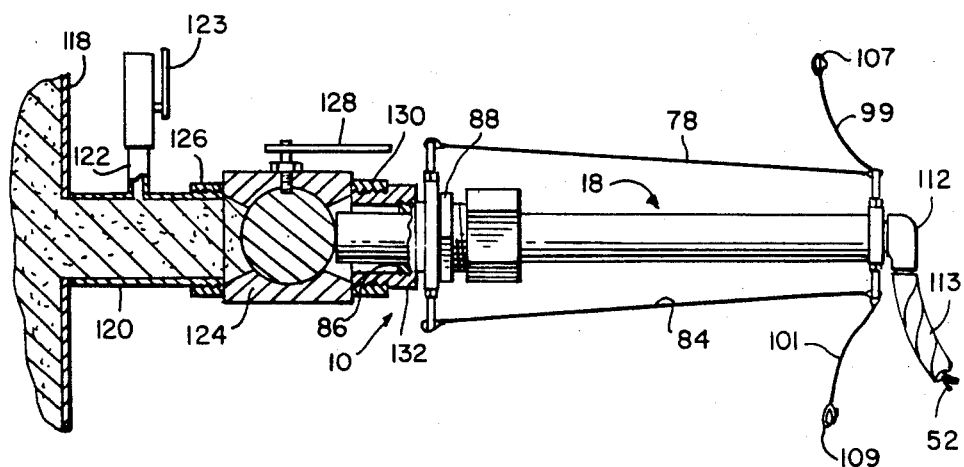
FIG. 3 is a side elevational view of the pH sensor system prior to insertion into a process flow line.
Figure 4:
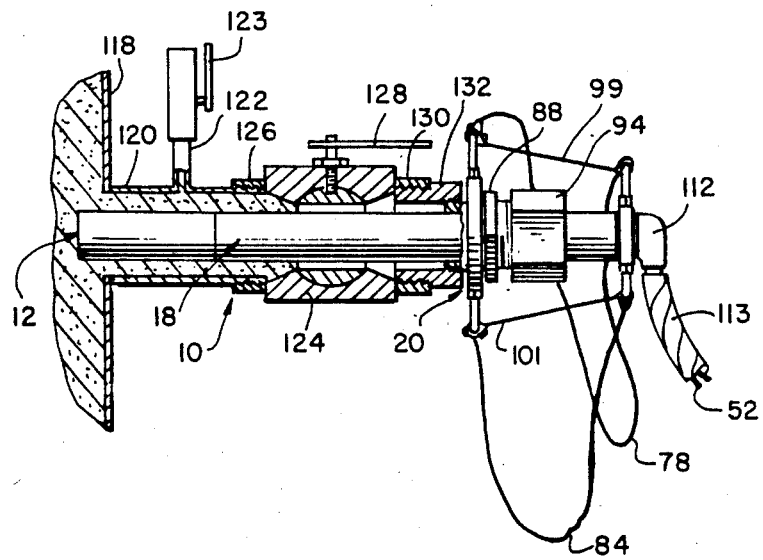
FIG. 4 is a side elevational view of the pH sensor system after insertion into the process flow line.

FIGS. 3 and 4 show generally the manner in which the sensor system 10 is deployed and then inserted into a process flow line without damaging the sensor electrode 14.

A fragment of a process pipe 118 is shown; however, it could also represent the wall of a vessel or a tank which may be lined with tile or may be unlined. The flow direction is suggested by arrows. A pipe nipple 120 is welded to the flow line and communicates therewith. A purge line 122 is welded or otherwise joined to nipple 120 for introducing water, at high pressure, into the purge line. The water flushes the nipple and dislodges any compacted mass or debris that may have entered the nipple. Purge water is only needed to clean the nipple before probe insertion. Valve 123 is used to turn purge water on or off.

A ball valve 124 is joined to nipple 120 by a threaded connection 126; the ball valve is shown in its closed position in FIG. 3 and in its opened position in FIG. 4. A manual operator 128 is manipulated to adjust the condition of the ball valve. A second threaded connection 130 engages a threaded reducer 132 secured to the ball valve 124. First collar 20 is seated on the tube fitting 22 abutting against shoulder 88. The threaded reducer, in turn engages the external threads on tapered seat section 86 of tube fitting 22. In this fashion, first collar 20, with associated restraint cables 78,84, is held captive to the process pipe structure via the contiguous mechanical connections formed by the pipe nipple 120, threaded connection 126, ball valve 124, threaded connection 130, threaded reducer 132, the engagement of the threaded reducer with lead section 86 of tube fitting 22 and shoulder 88. Restraint cables 78,84 are presently left hanging freely.

Second collar 26 is seated upon the remote end section 58 of insertion shaft 18 and abuts against the shoulder 68 defined between section 58 and the central section 54 of insertion shaft 18. Second collar 26 is retained in place by the attachment of conduit 112. Restraint cables 99 and 101 are presently left hanging freely. Retaining nut 24 is slid over the sheath 12 and insertion shaft 18 to a position adjacent to second collar 26.

The sensor system 10 must be slid through the opened ball valve 124 so that pH sensing electrode 14 projects through pipe nipple 120 and into location within the process flow line that will yield representative values. The process flow line may contain a slurry, or viscous syrupy material, a liquid suspension of fibers having high consistency, or a free flowing liquid; additionally, debris and the like may be present in the process flow pipe. The flow in the process flow pipe may or may not be under considerable pressure. The protective sheath 12 protects the sensing electrode 14, the internal BNC connection 40,51 and the holder assembly 16 from being damaged by impact from solid objects and further strengthens the sensor to resist the shearing and/or bending forces that act upon the inwardly protruding end of the sensor assembly.

The insertion sequence for sensor system 10 is discernible from FIGS. 3 and 4. With ball valve 124 closed, the probe is inserted into tube fitting 22 only far enough to permit attachment of restraint cables 78,84 to eyes 100,106 on second collar 26 by the use of clips 103,105. The length of identical restraint cables 78,84 is selected to hold the probe securely in position in tube fitting 22 in order to prevent probe ejection by process fluid pressure when the ball valve 124 is opened. Water under pressure is introduced through line 122 by rotating operator 123 on valve 122 to purge out any compacted mass or debris that may be in pipe nipple 120.

Operator 128 is then rotated so that the ball valve 124 is opened, and then a manually applied, axially directed force is imposed upon insertion shaft 18. The shaft slides through the bore of the opened ball valve 124 until the pH sensing electrode 14 and the protective sheath 12 project the desired distance into the process flow line. The desired distance for insertion into the line 118 may be indicated by a score line or other visible marking on the body of the insertion shaft 18 adjacent to the end of tube fitting 22. After the electrode 14 and sheath 12 have been properly positioned, in order to retain the sensor assembly 10 in proper position and to preclude the assembly from being forced, under pressure, from such position, restraint cables 99,101 are extended between collars 26 and 20. Clips 107,109 on the opposite ends of the cables 99,101 secure the cables within the eyes on the bolts secured to collar 20. Cables 99,101 are normally only secured to collar 26, as shown in FIG. 3, and are joined to collar 20 after the sensor system has been secured in operative position, as shown in FIG. 4. After the cables 99,101 are secured, the retaining nut 24 is advanced onto the trailing section 90 of fitting 22. Such action causes the retaining nut to bite into the insertion shaft and lock the sensor in fixed position. Collars 20, 26 and all restraint cables can be rotated freely about the radii of system 10 so as not to interfere with the tightening of retaining nut 24 with a wrench.

The foregoing description sets forth the preferred mode of practicing the instant invention. Undoubtedly, changes, revisions, and modifications will occur to the skilled artisan, which will not require the exercise of inventive skill. For example, the sensing electrode may measure process fluid variables other than pH, such as ion activity, conductivity, etc., and the sensor system may be utilized in conjunction with by-pass lines, holding tanks, vessels, etc. Consequently, the appended claims should be liberally construed in a manner consistent with the spirit of this invention, and should not be restricted to their literal terms.

We claim:

1. An instrument for measruing physical or chemical variables in a process flow stream, said instrument comprising:
    (a) an electrode comprising a cylindrical body, a substantially flat sensing surface at the forward end of said body, and coupling means formed at the rear end of said body,
    (b) an electrode holder assembly with an enlarged forward end to receive said coupling means of said electrode,
    (c) an elongated cylindrical rigid insertion shaft including a first end section connected to said electrode holder, a second end section, and a central section of slightly greater diameter,
    (d) external threads located on said first and second end sections, a first shoulder formed between said first end section and said central section of said insertion shaft, and a second shoulder formed between said second end section and said central section of said insertion shaft,
    (e) said instrument being characterized by a hollow cylindrical rigid metallic sheath having an internal diameter slightly greater than the external diameter of the body of said electrode,
    (f) internal threads formed near the rear end of said sheath,
    (g) said internal threads being advanced over the external threads on the first end section of said insertion shaft until said sheath abuts against said first shoulder on the first end section of said insertion shaft,
    (h) said substantially flat sensing surface on said electrode being substantially flush with the forward end of said sheath, and
    (i) said cylindrical body of said electrode fitting within the forward end of said sheath, whereby said sheath completely surrounds and protects the body of said electrode, said coupling means, and said electrode holder assembly.

2. An instrument as defined in claim 1 wherein an O-ring is affixed to the exterior of the body of said electrode, and a step is defined in the interior of said sheath near its forward end, said O-ring contacting said step when said sheath is slid over said electrode to retain said electrode in a fixed snug position and prevent intrusion of process fluid into the interior of the instrument.

3. A sensor system for measuring physical or chemical variables in a process flow stream, said system comprising:
    (a) an electrode comprising a cylindrical body, a substantially flat sensing surface at the forward end of said body, and coupling means formed at the rear end of said body,
    (b) an electrode holder assembly with an enlarged forward end to receive said coupling means of said electrode,
    (c) an elongated cylindrical rigid insertion shaft including a first end section, a second end section, and a central section of slightly greater diameter than said end sections,
    (d) shoulders formed between said end sections and said central section of said shaft, and external threads defined on said end sections, (e) a hollow cylindrical rigid metallic sheath with threads defined on its interior surface, (f) said sheath being screwed into engagement with the threads on one end section of said insertion shaft until said sheath abuts against one of said shoulders, (g) a tube fitting comprising a leading section, a shoulder, and a trailing section, and further having an axially extending bore, the internal diameter of said bore being greater than the external diameter of the central section of said cylindrical insertion shaft, (h) a first collar having an annular body with a central opening, the diameter of said central opening being greater than the external diameter of said leading section of said fitting so that said first collar can be positioned thereupon, (i) a second collar having an annular body with a central opening, the diameter of said central opening being greater than that of said second end section of said insertion shaft so that said second collar can be positioned thereupon, and (j) a first pair of restraint cables extending between said first and second collars to prevent accidental ejection of the sensor system during insertion into the process flow stream.

4. A sensor system as defined in claim 3 wherein eye-bolts are secured to each of said collars, and said first pair of restraint cables is secured to said eye-bolts.

5. A sensor system as defined in claim 3 further comprising a second pair of restraint cables, said second pair of restraint cables being shorter than said first pair of restraint cables, and said second pair of restraint cables being secured between said first and second collars when said first pair of restraint cables is rendered ineffective.

6. A sensor system as defined in claim 3 wherein said second collar is positioned on one end section of said insertion shaft to abut against the shoulder on the shaft defined between one end section and the central body section of said shaft.

7. A sensor system as defined in claim 3 wherein the leading section of the tube fitting is tapered, and said first collar abuts against said shoulder of said tube fitting.

* * * * *